United States Patent [19]

Shillington et al.

[11] 4,454,944
[45] Jun. 19, 1984

[54] ONE WAY SHARPS RECEPTACLE

[76] Inventors: Richard A. Shillington, 1291 Clayford Ave., Westlake Village, Calif. 91361; Alec Oberschmidt, 1368 Hymettus, Leucadia, Calif. 92024

[21] Appl. No.: 362,875

[22] Filed: Mar. 29, 1982

[51] Int. Cl.³ .................... A61M 5/32; B02C 19/12
[52] U.S. Cl. .................... 206/366; 206/63.5; 206/525; 206/380; 220/94 A; 220/18; 248/312
[58] Field of Search .................... 206/366, 63.5, 525, 206/380; 215/100 A, 1 C; 220/94 A, 404, 18; 248/312

[56] References Cited

U.S. PATENT DOCUMENTS

| | | | |
|---|---|---|---|
| 1,714,048 | 5/1929 | Reeder | 248/312 |
| 2,034,006 | 3/1936 | Smith | 206/63.5 |
| 3,207,359 | 9/1965 | Heisler et al. | 220/94 A |
| 3,381,814 | 5/1968 | Benfield | 206/63.5 |
| 3,410,459 | 11/1968 | Conley | 215/100 A |
| 3,556,293 | 1/1971 | Schlueter | 206/525 |
| 3,765,574 | 10/1973 | Urquiza | 220/404 |
| 4,351,434 | 9/1982 | Elisha | 206/366 |

Primary Examiner—William T. Dixson, Jr.
Attorney, Agent, or Firm—Brown & Martin

[57] ABSTRACT

A disposable receptacle for disposing of sharp and hazardous objects such as syringes, razor blades and similar objects discarded from clinics and hospitals, includes a generally box-like container preferably constructed of a rigid durable plastic having a circular opening in the top with a neck projecting from the opening and including a closure having a plurality of pie-shaped spring flaps forming a one way closure for permitting the insertion of objects but preventing the withdrawal of objects from the container. Shoulders project upward from the top of the container at each side of the neck with handles extending between the neck and shoulders providing handles for carrying, and forming slots therebetween for receiving a generally D-shaped lock strap member for lockably attaching the container to a vertical support surface preferably at an elevated position to reduce access by children and the like. Grooves are formed around the perimeter of the container for receiving straps for mounting the container.

12 Claims, 6 Drawing Figures

ONE WAY SHARPS RECEPTACLE

BACKGROUND OF THE INVENTION

The present invention relates to security containers and pertains particularly to a disposable security container for receiving sharp and hazardous objects or articles for disposal and for frustrating access thereto.

Hospitals and clinics utilize a great number of disposable syringes, cutting instruments such as razor blades and the like and other similar disposable hazardous objects. The disposition of such objects and articles to prevent them from falling into the hands of children, or others who might accidentally misuse or injure themselves with such articles, is a long-standing problem. It is desirable that a disposable container be available which is inexpensive to manufacture, yet durable enough and have means to prevent ready acceass thereto. It is also desirable that such means be available for securely locking the container to prevent unauthorized removal thereof.

SUMMARY AND OBJECTS OF THE INVENTION

It is the primary object of the present invention to provide an improved disposable container for hazardous articles.

In accordance with the primary aspect of the present invention, a sharp or hazardous article disposable container is constructed of an inexpensive, durable, lightweight material and includes an access opening permitting the insertion of disposable objects and restricting access to the interior of the container for removal of such objects. Another aspect of the invention includes locking means for locking the container to a secure anchoring system.

BRIEF DESCRIPTION OF THE DRAWINGS

The above and other objects and advantages of the present invention will become apparent from the following description when read in conjunction with the drawings wherein.

DETAILED DESCRIPTION OF A PREFERRED EMBODIMENT

Figure 1:
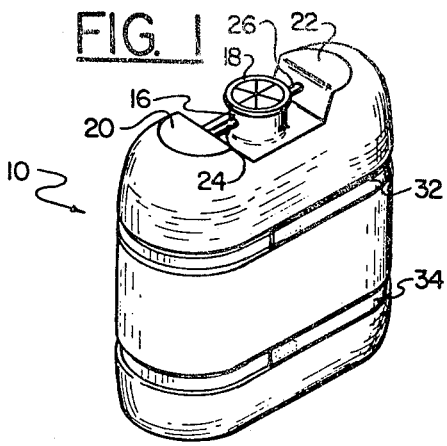
FIG. 1 is a perspective view of a disposable container in accordance with the invention.

Turning to the drawings, there is illustrated a container designated generally by the numeral 10, having a generally flat bottom 12 with a continuous upstanding sidewall 14 extending upward therefrom to a top which includes a centrally located neck 16 with an opening at the upper end thereof covered by a closure member 18. Extending upward adjacent to each side of the neck 16 is a pair of shoulders 20 and 22 which include flat horizontal portions for stacking of containers on top of one another. Extending between the neck and each of the shoulders on each side is a pair of handles 24 for grasping and carrying the container and also for providing means for security anchoring of the container as will be described.

The container is preferably blow-molded of a suitable durable plastic material of high strength and durability, yet light and sufficiently inexpensive for disposal. The illustrated shape permits it to be blow-molded and retain a uniform thickness preferably on the order of about 0.040 thousandths or one millimeter. The container is preferably of a size to receive and accommodate the largest of syringes utilized in clinics and hospitals. The container is primarily for use in the disposal of sharp and hazardous objects and instruments from hospitals and clinics and the like. Such objects and things are typically referred to in the trade as Sharps. These objects include syringes, razor blades and the like and present a problem of disposal to prevent them from falling into the hands of children and unauthorized users thereof.

Figure 2:
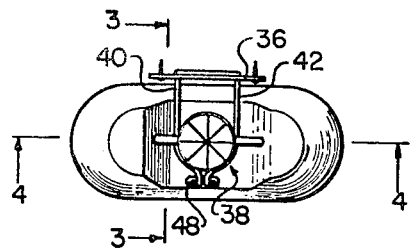
FIG. 2 is a top plan view of the embodiment of FIG. 1.

The container has a capacity on the order of about two gallons and is configured to have a generally oval plan view cross section as seen in FIG. 2 defined by generally flat front and back walls and semi-cylindrical end walls and a generally rectangular front and side view cross sections. The width of the container defined by the space between the generally semi-cylindrical end walls is on the order of about nine inches and about four to four and one-half inches thick defined by the distance between the front and back walls and about twelve to fourteen inches high. This provides a container sufficiently high and with a width that accommodates the largest of syringes typically used today. The neck 16 has a length that is on the order of about between two and three inches, which eliminates or at least reduces the hazard of a syringe falling into the container and turning upward with the point thereof closely adjacent the closure such that attempt to insert another syringe or disposable object results in puncturing the hand or fingers. The neck is on the order of approximately two and one-half inches in diameter with the closure opening itself being on the order of approximately two and one-eighth inches in diameter at the opening.

Figure 3:
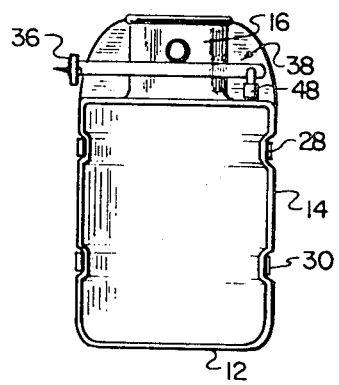
FIG. 3 is a side elevational view in section taken generally on lines 3—3 of FIG. 2.

The body of the container as seen in FIG. 1 and 3 include a pair of grooves consisting of an upper groove 28 and a lower groove 30 molded or formed therein for receiving upper mounting strap 32 and the lower mounting strap 34 and also for reinforcing the walls of the container. These mounting straps are preferably flexible straps with hook and loop-type faasteners such as sold under the Mark "Velcro" or other suitable latch or fastening means for quick mounting and release of the container such as from a mounting panel or wall or the like. Preferably the container is mounted on a wall or other vertical support means at a distance above the floor to prevent access to the opening therein by children and the like.

The neck 16 and handles 24 and 26 between the neck and shoulders provide means for additional security of the container. This permits the use of a locking device as illustrated in FIGS. 2 and 3 for locking the container to a support structure such as a wall or upstanding support preferably at a convenient height for use yet at a height inaccessible to children.

The locking device comprises a base, bar or plate 36 having a pair of spaced apart holes through which the curved ends of a generally D-shaped strap 38 extend with hook or arm portions 40 and 42 extending through the holes in the bar 36 and around opposite sides of the neck of the container. The locking member of a padlock or the like 48 extends through aligned holes in the outer adjacent terminal ends of the two arm portions 40 and 42. This locks the two arms in place around neck 16 of the container until the padlock is removed, which permits removal of the bars and removal of the container 10. This provides a security measure that prevents the container from being removed by unauthorized persons.

Figure 5:
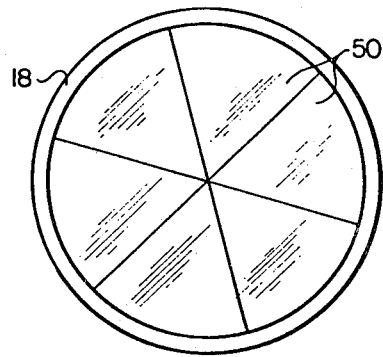
FIG. 5 is a top plan enlarged view of the closure of the container.
Figure 6:
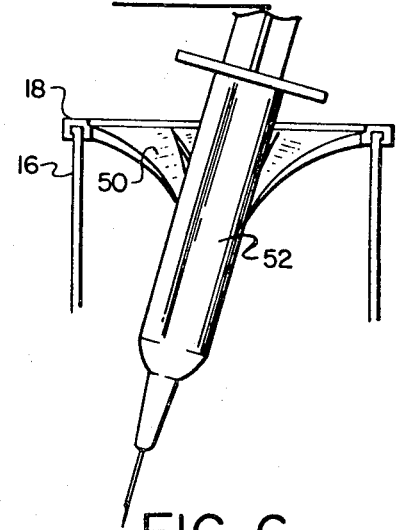
FIG. 6 is an enlarged detail view in section of closure and neck of the container.

Details of the closure are best shown in FIGS. 5 and 6. The closure 18 preferably comprises a substantially flat disk of a material having a memory or spring-like characteristics. With such material, the many pie-shaped flaps of the closure return to their original closed configuration after being deformed or pushed aside for insertion of an article or object into the container.

Figure 4:
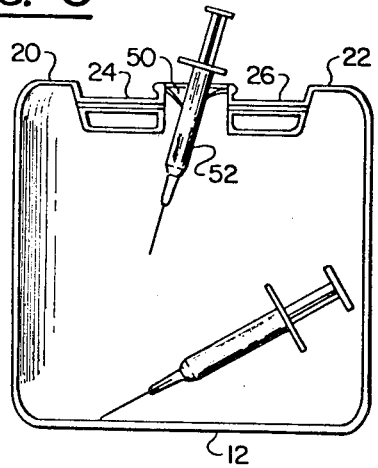
FIG. 4 is a front elevational view in section taken generally on lines 4—4 of FIG. 2.

The cover may be removable or may be nonremovably secured to the container as desired. The closure comprises a disk-like structure slit along radial lines forming a plurality of pie-shaped flaps 50. These flaps as best seen in FIGS. 4 and 6 deform downward to permit the insertion of an object such as a syringe or the like 50 into the neck of the container. Preferably the container neck is of sufficiently small diameter .pa (on the order of about 2 inches or 50 millimeters) that the average adult cannot insert a hand into the container. However, due to the necessity of making the opening in the closure 18 large enough to accept the largest syringe to be discarded, it will be large enough that a child's hand may be inserted into the container. The length of the neck provides some space to prevent the hand from coming into immediate contact with needles and objects within the container. Additionally, the flap structure of the closure will tend to discourage attempts to gain access to the container.

While we have illustrated and described our invention by means of specific embodiments, it is to be understood that numerous changes and modifications may be made therein without departing from the spirit and scope of the invention as defined in the appended claims.

We claim:

1. A container for disposing of hazardous articles, said container comprising:
    a top, a generally flat bottom, and a continuous peripheral wall defining a generaly flat front and back walls and semi-circular end walls interconnecting the top and bottom for defining a container having a width defined by the distance between the end walls greater than the thickness defined by the distance between the front and back walls, said top including an opening proximate the center thereof and an elongated generally cylindrical neck communicating with and extending upwardly terminating in an outer open end spaced from the opening, and
    a one way closure covering the outeropen end of said neck.

2. The container of clam 1 wherein:
    said closure comprises a generally flat circular disk of flexible material having a memory and a plurality of generally pie shaped flaps extending from the periphery thereof to a point at the center thereof.

3. The container of claim 1 wherein said top includes a pair of shoulder projecting upward therefrom, one shoulder on each side of said neck and each shoulder including a flat surface in the plane of the closure for defining a support surface for stacking a plurality of said containers.

4. The container of claim 3 further comprising handle means extending from said neck to each of said shoulders.

5. The container of claim 4 wherein the height and width of said container are about equal and the thickness is between about one-third and one-half the width.

6. The container of claim 5 wherein the length of said neck is about equal to the diameter thereof.

7. The container of claim 6 in combination with locking means for locking said container to a support structure, said locking means comprising a fixed bar having a pair of spaced apart holes, and
    a generally D-shaped strap extending through the holes in the bar and having arm portions which extend around generally opposite sides of the neck of the container, the arm portions having adjacent terminal ends with aligned holes extending therethrough for receiving a locking member.

8. The container of claim 4 wherein said shoulders are spaced from said neck, and
    said handle means comprises a generally cylindrical member extending generally horizontally from each side of said neck to each of said shoulders.

9. The container of claim 8 including a pair of spaced apart band receiving grooves formed in and extending around the perimeter of said container walls.

10. A container for disposing of hazardous articles, said container comprising:
    a generally flat bottom, a top including an opening proximate the center thereof and an elongated generally cylindrical neck communicating with and extending upward from the opening terminating in an outer open end spaced from the opening, said top further including a pair of shoulders projecting upward therefrom, one shoulder on each side of said neck and each should including a flat surface in the plane of the closure for defining a support surface for stacking a plurality of said containers, and
    a continuous peripheral wall interconnecting the top and bottom for defining a container, and
    a one way closure covering the outer open end of said neck.

11. The container of claim 10 wherein said shoulders are spaced from said neck, and further comprising a generally cylindrical member extending generally horizontally from each side of said neck to each of said shoulders for defining handle means.

12. The container of claim 11 in combination with locking means for locking said container to a support structure, said locking means comprising a fixed bar having a pair of spaced apart holes and,
    a generally D-shaped strap extending through the holes in said bar and having arm portions which extend around opposite sides of the neck of the container, the arm portions having adjacent terminal ends with aligned holes extending therethrough for receiving a locking member.

* * * * *